United States Patent [19]

Shapland et al.

[11] Patent Number: 5,282,785
[45] Date of Patent: Feb. 1, 1994

[54] DRUG DELIVERY APPARATUS AND METHOD

[75] Inventors: James E. Shapland; Mark B. Knudson, both of Shoreview; Jin Shimada, Falcon Heights, all of Minn.; Keith R. Hildebrand, Houlton, Wis.

[73] Assignee: CorTrak Medical, Inc., Roseville, Minn.

[21] Appl. No.: 956,789

[22] Filed: Oct. 5, 1992

Related U.S. Application Data

[63] Continuation-in-part of Ser. No. 937,464, Aug. 28, 1992, which is a continuation-in-part of Ser. No. 705,731, May 24, 1991, which is a continuation-in-part of Ser. No. 637,299, Jan. 3, 1991, abandoned, which is a continuation-in-part of Ser. No. 538,961, Jun. 15, 1990, abandoned.

[51] Int. Cl.$^5$ .............................. A61B 17/36
[52] U.S. Cl. ........................ 604/21; 604/20; 604/96
[58] Field of Search ................... 604/20-22, 604/96-103, 52-53; 128/24 AA

[56] References Cited

U.S. PATENT DOCUMENTS 578,611  3/1897  Rively .

(List continued on next page.)

FOREIGN PATENT DOCUMENTS

| | | |
|---|---|---|
| 299698 | 1/1989 | European Pat. Off. . |
| 372088 | 6/1990 | European Pat. Off. . |
| 147314 | 4/1981 | German Democratic Rep. . |
| 49-132888 | 12/1974 | Japan . |
| WO89/01794 | 3/1989 | PCT Int'l Appl. . |
| WO91/16945 | 11/1991 | PCT Int'l Appl. . |
| 588870 | 6/1977 | Switzerland . |
| 1003853 | 3/1983 | U.S.S.R. ............... 604/20 |
| 1069826 | 1/1984 | U.S.S.R. . |
| 1069827 | 1/1984 | U.S.S.R. . |
| 1410973 | 7/1988 | U.S.S.R. . |

OTHER PUBLICATIONS

Antich, *Journal of Orthopaedic and Sports Physical Therapy,* 4(2), 99-102 (1982).
Brand, *Cardio,* Nov., 48-56 (1989).
Ellman et al., *Investigative Radiology,* 19(5), 416-423 (1984).
Goldman et al., *Atherosclerosis,* 65, 215-225 (1987).
Jorgensen et al., *The Lancet,* May 20, 1106-1108 (1989).
Klimberg et al., *Urology,* 33(2), 153-158 (1989).
Layer et al., *Br. J. Surg.,* 71, 709-710 (1984).
Okada et al., *Stroke,* 19(12), 1470-1476 (1988).
Okada et al., *Neurosurgery,* 25(6), 892-898 (1989).
Sheehan and Hrapchak, *Theory and Practice of Histotechnology,* Ch. 2, 40-50 (1984).
Skauer, et al., *International Journal of Pharmaceutics,* 20, 235-245 (1984).
Wolinsky et al., *JACC,* 15(2), 475-481 (1990).
*BBI Newsletter,* 13(5), 85-91 (1990).

*Primary Examiner*—C. Fred Rosenbaum
*Assistant Examiner*—Michael Rafa
*Attorney, Agent, or Firm*—Merchant, Gould, Smith, Edell, Welter & Schmidt

[57] ABSTRACT

A drug delivery apparatus and method for delivering a drug locally to internal body tissue. The invention contemplates positioning a drug delivery device in a body passageway or within body tissue and then selectively introducing a selected drug so that it is transported across a drug transport wall of the device for direct contact with the passageway wall or body tissue. A further aspect of the present invention involves treating a dilated vessel in the area of a stenotic lesion with a fixative or other drug to render the vessel biologically inert and to form a biological stent or prevent restenosis using specifically selected drugs. A still further aspect of the present invention involves treating a tumor or local or regional tissue mass with antitumor sensitizing agents, biological modifiers, antibiotics or other types of drugs by delivery of the drug to the tumor or tissue area directly or through the passageway wall.

21 Claims, 4 Drawing Sheets

U.S. PATENT DOCUMENTS

| | | |
|---|---|---|
| 725,731 | 4/1903 | Linn . |
| 873,021 | 12/1907 | Cool . |
| 2,123,980 | 7/1938 | Warwick . |
| 2,499,045 | 8/1948 | Walker et al. . |
| 3,542,014 | 11/1970 | Peronneau . |
| 3,865,108 | 2/1975 | Hartop . |
| 4,126,134 | 11/1978 | Bolduc et al. . |
| 4,137,906 | 2/1979 | Akiyama et al. . |
| 4,202,346 | 5/1980 | Granier . |
| 4,323,071 | 4/1982 | Simpson et al. . |
| 4,338,942 | 7/1982 | Fogarty . |
| 4,364,392 | 12/1982 | Strother et al. . |
| 4,383,529 | 5/1983 | Webster . |
| 4,403,612 | 9/1983 | Fogarty . |
| 4,411,648 | 10/1983 | Davis et al. . |
| 4,416,274 | 11/1983 | Jacobsen et al. . |
| 4,417,576 | 11/1983 | Baran . |
| 4,423,725 | 1/1984 | Baran et al. ............................ 604/43 |
| 4,456,012 | 6/1984 | Lattin . |
| 4,509,523 | 4/1985 | Pevsner . |
| 4,551,132 | 11/1985 | Pasztor et al. . |
| 4,573,966 | 3/1986 | Weikl et al. . |
| 4,582,181 | 4/1986 | Samson . |
| 4,606,337 | 8/1986 | Zimmermann et al. . |
| 4,608,984 | 9/1986 | Fogarty . |
| 4,610,662 | 9/1986 | Weikl et al. . |
| 4,636,195 | 1/1987 | Wolinsky . |
| 4,689,041 | 8/1987 | Corday et al. . |
| 4,693,704 | 9/1987 | Ogita . |
| 4,698,058 | 10/1987 | Greenfeld et al. . |
| 4,705,507 | 11/1987 | Boyles . |
| 4,714,460 | 12/1987 | Calderon . |
| 4,733,665 | 3/1988 | Palmaz . |
| 4,744,366 | 5/1988 | Jang . |
| 4,767,402 | 8/1988 | Kost et al. . |
| 4,776,337 | 10/1988 | Palmaz . |
| 4,787,888 | 11/1988 | Fox . |
| 4,800,882 | 1/1989 | Gianturco . |
| 4,819,637 | 4/1989 | Dormandy, Jr. et al. . |
| 4,819,751 | 4/1989 | Shimada et al. . |
| 4,824,436 | 4/1989 | Wolinsky . |
| 4,832,688 | 5/1989 | Sagae et al. . |
| 4,866,050 | 9/1989 | Ben-Amoz . |
| 4,948,587 | 8/1990 | Kost et al. . |
| 4,994,033 | 2/1991 | Shockey et al. . |
| 5,000,734 | 3/1991 | Boussignac et al. . |
| 5,007,897 | 4/1991 | Kalb et al. . |
| 5,041,107 | 8/1991 | Heil, Jr. ............................ 604/891.1 |
| 5,087,243 | 2/1992 | Avital . |
| 5,087,244 | 2/1992 | Wolinsky et al. . |
| 5,102,402 | 4/1992 | Dror et al. . |
| 5,236,413 | 8/1993 | Feiring ............................ 604/21 |

DRUG DELIVERY APPARATUS AND METHOD

REFERENCE TO CO-PENDING APPLICATION

This application is a continuation-in-part of U.S. patent application Ser. No. 07/937,464, filed Aug. 28, 1992, which is a continuation-in-part of U.S. patent application Ser. No. 07/705,731, filed May 24, 1991, which is d continuation-in-part of U.S. patent application Ser. No. 637,299, filed Jan. 3, 1991ABN, which in turn is a continuation-in-part of U.S. patent application Ser. No. 538,961, filed Jun. 15, 1990ABN.

BACKGROUND OF THE INVENTION

1. Field of the Invention

The present invention relates generally to a drug delivery apparatus and method, and more particularly, to an apparatus and method for selectively and locally delivering a drug to internal body tissue.

2. Description of the Prior Art

Many techniques currently exist for delivering drugs or other medicaments to body tissue. These include, among possible others, oral administration, injection directly into body tissue such as through an intramuscular injection or the like, topical or transcutaneous administration where the drug is passively absorbed, or caused to pass, into or across the skin or other surface tissue and intravenous administration which involves introducing a selected drug directly into the blood stream.

Except for topical or transcutaneous administration, the above drug delivery systems tend to be systemic. In other words, administration of the drug is delivered throughout the body by the blood stream.

Over the past several years, the pursuit of devices for localized drug delivery has become exceedingly more intense as the advantages of this method of therapy over systemic drug administration have become apparent. Because many diseases affect a specific site or organ within the body, it is advantageous to preferentially treat the affected area. This avoids high systemic drug levels which may result in adverse side effects and concentrates therapeutic agents in the local area where they are needed. By treating just the diseased tissue, the total quantity of drug used may be significantly reduced, and hence the cost of therapy, especially when using newer genetically engineered drugs. Moreover, local drug delivery may allow for the use of certain effective therapeutic agents which have previously been considered too toxic or nonspecific to use systemically.

Several devices have been developed for the purpose of accessing specific body lumens or passageways (i.e., blood vessels, gastrointestinal tract, urinary tract) and delivering therapeutic agents transmurally to specific subregions of tissue. A double-balloon catheter has been used to administer agents to the area confined by the balloons. A disadvantage of this system is that drugs may be lost through communicating vessels between the balloons. Alternatively, a perforated balloon has been developed to deliver agents directly into the vessel wall. A major disadvantage with both of these systems in certain desired applications is that the drug is delivered radially in all directions.

In some therapeutic applications, it can be advantageous to deliver the drug only to one radial section of the vessel or passageway. For example, localized neoplasia in the gastrointestinal, urinary or reproductive tracts often encompass only a portion of the lumenal circumference. The ducts of the prostate gland communicate with the floor of the urethra; therefore, it would be more efficient to deliver agents (antibiotics, anticancer agents) toward the ducts which access the prostate than to circumferentially deliver across the prostatic urethra.

Therefore, a need exists for a drug delivery apparatus providing radially restricted delivery of a drug or medicant to a localized area of internal body tissue.

SUMMARY OF THE INVENTION

In accordance with the present invention, an apparatus and method is provided for delivering a drug or combination of drugs selectively and locally to an internal body tissue. The invention relates to an apparatus and method for radially restricted delivery of a drug or combination of drugs substantially transversely to the longitudinal axis of a body passageway such as blood vessel, urinary tract, intestinal tract, reproductive tract, etc., in order to treat a localized region of the passageway itself or to treat d localized region or tissue located adjacent to the passageway.

In the preferred embodiment, the apparatus includes a flexible member adapted for insertion into a target area of internal tissue, such as a passageway or vessel, a drug delivery means including a drug delivery chamber connected with said member for delivering a drug to a target area, and a nonpermeable balloon secured to and about or above the drug delivery chamber for securing the apparatus against internal tissue. In accordance with the invention, the nonpermeable balloon radially restricts local delivery of a drug to an internal body tissue.

The drug delivery means further includes a fluid delivery lumen or passageway extending from the proximal end of the flexible catheter to the drug chamber for delivering a selected drug to the drug chamber. The drug chamber defines a drug delivery area and has a drug transport wall which is constructed of a material that permits selective transport of a drug therethrough, i.e. constructed of at least perforated, permeable, microporous or semipermeable material through which the drug is intended to selectively pass, that is, selectively permeable.

Transport of the drug across the drug transport wall can be facilitated by a driving force such as pressure, iontophoresis or phonophoresis. In preferred embodiments, non-pressure transport forces such as iontophoresis or phonophoresis are employed.

In one embodiment, the apparatus includes circumferential lips immediately adjacent the proximal and distal ends of the drug delivery area that act to minimize movement of a drug beyond the segment of vessel or hollow organ to be treated. An embodiment of the radially restricted local delivery apparatus can also have a drug recovery lumen extending from the drug chamber to the proximal end of the flexible catheter.

Accordingly, it is an object of the present invention to provide a drug delivery apparatus and method for radially restricted delivery of a drug or combination of drugs locally to internal body tissue.

This object of the present invention will become apparent with reference to the drawings, the description of the preferred embodiment and method, and the appended claims.

DESCRIPTION OF THE DRAWINGS

FIGS. 6a and 6b show a cross-section of selectively permeable microporous membrane of a catheter according to the present invention.

DESCRIPTION OF THE PREFERRED AND ALTERNATE EMBODIMENTS AND METHODS

FIGS. 1-9 illustrate preferred and alternate designs of the drug delivery apparatus in accordance with the present invention. In general, this apparatus provides a means and a system for delivering a drug or combination of drugs to or through a localized area of internal body tissue, such as a passageway or hollow organs, radially restricted to less than 360° in order to treat the localized area of tissue or to treat a localized area of tissue located adjacent to the passageway, with minimal, if any, undesirable effect on other body tissue.

The device is designed to eliminate the disadvantages of the currently developed devices described above. The major advantage of this device is that it allows for radially restricted and localized drug delivery across a body passage or vessel. Another advantage is that the balloon and drug reservoir are indeed separate components so that pressure used to inflate the balloon is not transferred to the drug solution. This may be especially important when active methods of drug delivery such as iontophoresis or phonophoresis are desired without the additive effects of pressure delivery.

The drug delivery apparatus includes a unique balloon and drug delivery chamber design which can be used in conjunction with existing catheters. The term catheter as used in the present application is intended to broadly include any medical device designed for insertion into a body passageway to permit injection or withdrawal of fluids, to keep a passage open or for any other purpose. It is contemplated that the drug delivery apparatus of the present invention has applicability for use with any body passageways including, among others, blood vessels, urinary tract, intestinal tract, reproductive tract, respiratory tract, hollow organs and the like.

Figure 1:
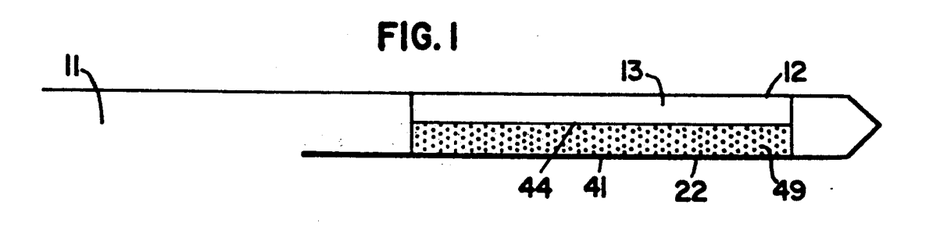
FIG. 1 is a fragmentary view, partially in section, of a first embodiment of the drug delivery apparatus of the present invention in the form of a catheter with a modified dilatation balloon in its deflated state.

FIG. 1 illustrates the distal end of a catheter with a drug delivery apparatus according to the present invention, with a balloon 12 in a deflated state. The catheter can include a guide wire (not shown); an elongated, flexible catheter body 11; a drug delivery means having a drug delivery chamber 49 with a drug delivery area 41 including a selectively permeable outer wall or boundary layer 22; and a balloon 12 positioned on the catheter body 11 above or about a portion of the drug delivery chamber 49. The catheter body 11 has a balloon lumen or passageway (seen best in FIGS. 7-9) extending along the catheter body 11 to the proximal end of the body 11 for inflation and deflation of the balloon 12. The balloon 12 is affixed to or secured about drug chamber 49 at wall 44 by known techniques, such as adhesives, laser welding, or, preferably, ultrasonic or radio frequency welding, or the like. In a preferred embodiment, the material from which the drug delivery area boundary layer or outer wall 22 is constructed is a permeable or semipermeable material which is effective to permit transport or passage of the fixative or other drug across the balloon surface as a result of an appropriate driving force.

Figure 2:
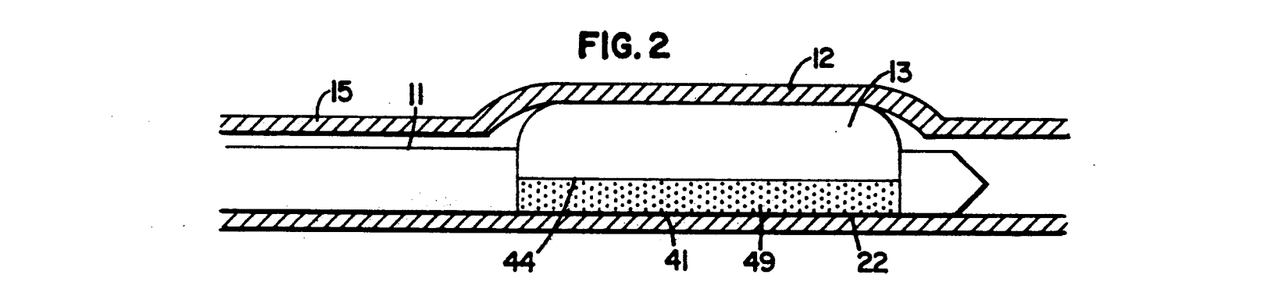
FIG. 2 is a fragmentary view, partially in section, of the drug delivery apparatus of FIG. 1 positioned in a blood vessel with the dilatation balloon in its inflated state.

FIG. 2 further illustrates the drug delivery apparatus of FIG. 1 with the balloon 12 in its inflated state within a body passageway in which the vessel walls are indicated by the reference numeral 15.

Figure 7:
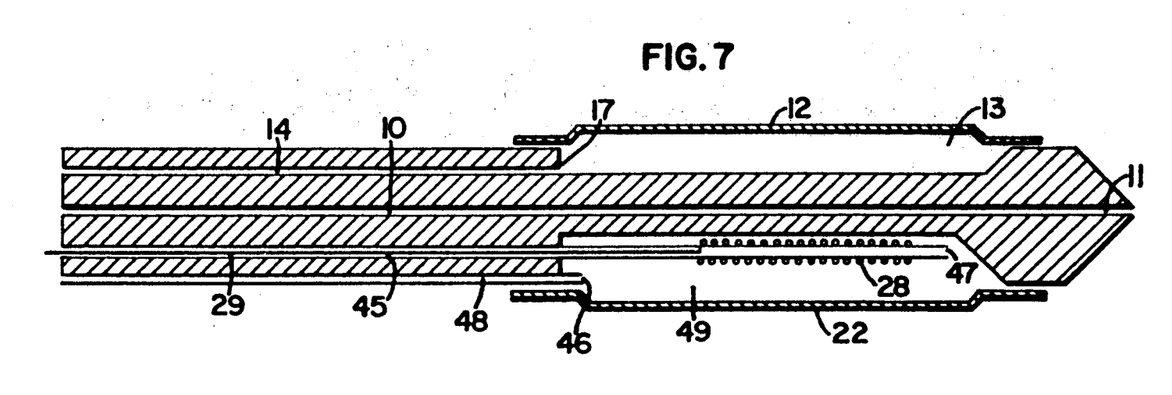
FIG. 7 is a fragmentary view of a modified iontophoretic embodiment of the drug delivery apparatus of the present invention.
Figure 8:
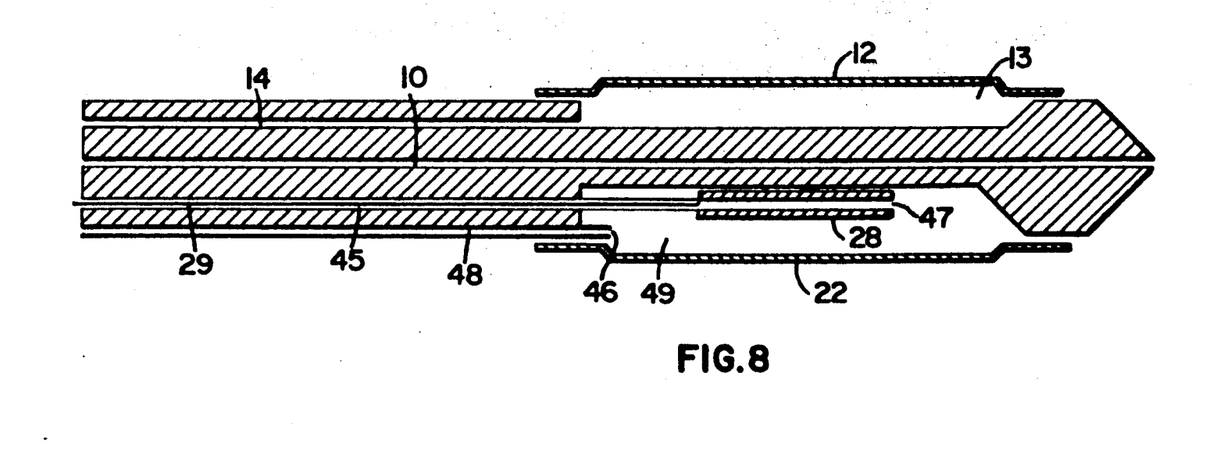
FIG. 8 is a fragmentary view of a modified phonophoretic embodiment of the drug delivery apparatus of the present invention.
Figure 9:
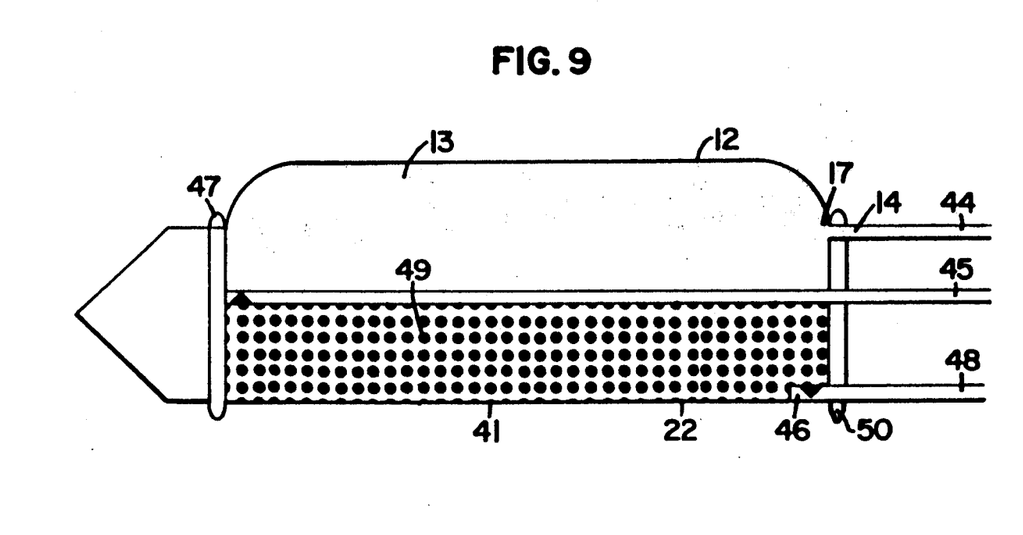
FIG. 9 is a fragmentary view of an alternate embodiment of the present invention showing drug delivery area isolating retention lips.

As shown in FIGS. 1 and 2, the delivery end of the catheter 11 has an expandable balloon or hemiballoon 12 that restricts a localized area for drug delivery and a drug reservoir 49 with an associated boundary layer or selectively permeable outer wall 22 interfacing between the drug solution and the targeted tissue. The balloon 12 is nonpermeable. It may be composed of either an elastic or nonelastic (fixed maximal volume) material. Non-limiting examples of materials for the balloon include impermeable materials such as polyethylene, polyester, polyurethanes, polyvinyl chloride, as well as natural and synthetic elastomers or the like understood by those skilled in the art. Referring to FIGS. 7-9, single lumen 14 communicates between the balloon 12 and the inflation port 17 of the catheter. The balloon, when expanded with air or fluid, provides intimate contact between the delivery area 41 of drug chamber 49 and the targeted tissue.

Juxtaposed to the balloon 12 is delivery region 41 of catheter 11 containing the drug chamber 49 and the boundary layer or selectively permeable membrane 22 interfacing between the drug solution and the targeted tissue. The selectively permeable boundary layer 22 could be simply a continuation of the catheter body 11 with small holes (0.5-5 mm) for drug transfer. Alternatively, a semipermeable or microporous membrane with submicron holes could be utilized to further restrict passive drug transfer. The particular design of the boundary layer (degree of porosity) would depend on the particular clinical situation (e.g., it may be desirable to have minimal pore size and hence minimal fluid leakage when delivering drugs into an artery wall).

Preferably, as best seen in FIGS. 7 and 8, drug chamber 49 is supplied with both an influx 45 and efflux lumen 48 so that drug may be circulated, providing constant high concentrations of drug molecules within the delivery area. Another advantage of the dual lumen design is that air can be easily and completely evacuated from the reservoir when filling.

Figure 5:
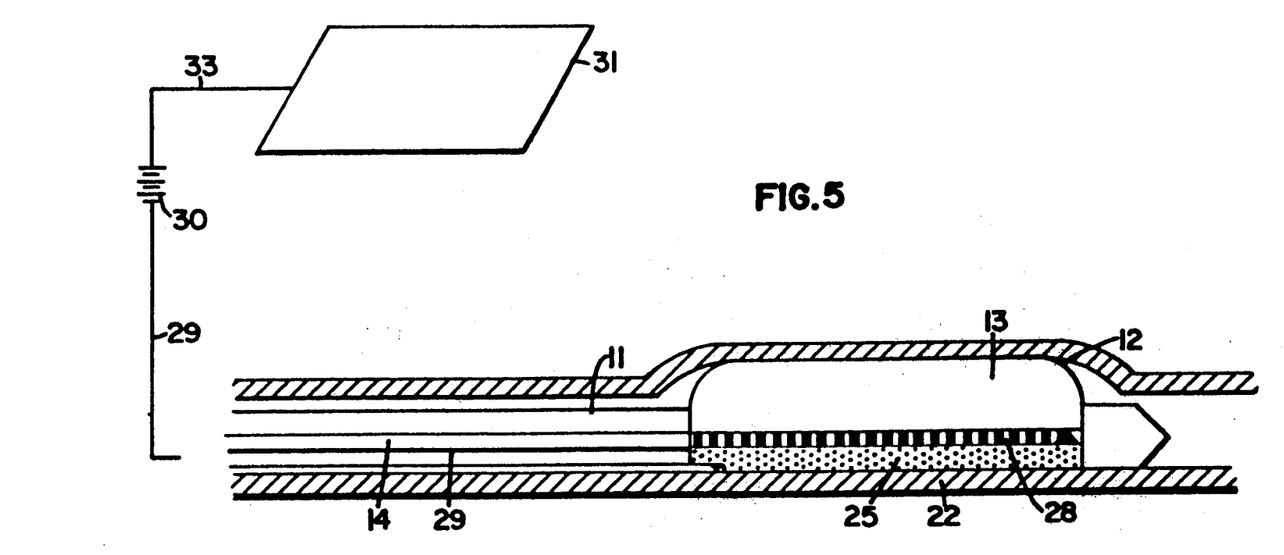
FIG. 5 is a fragmentary view, partially in section, of the drug delivery apparatus of the present invention positioned in a blood vessel and embodying iontophoresis means to transport the drug across the balloon surface.

In a preferred embodiment, the drug chamber 49 includes an active delivery element 28 for a non-pressure driving force (i.e., electrode for iontophoresis, transducer for phonophoresis) best seen in FIGS. 5, 7, and 8. Alternatively, in the absence of the above-mentioned active delivery elements, pressure could also be utilized to move drug into the tissue. The delivery methods (iontophoresis, phonophoresis, pressure) could also be used in various combinations with a catheter so equipped with the necessary "driver" elements to optimize local drug delivery for a particular clinical situation.

Referring to FIG. 9, circumferential "lips" (protruding ridges of plastic) 50 are located immediately proximal and distal to the delivery region 41 of the drug chamber 49 of catheter 11. The circumferential lips 50 act to minimize movement of drug beyond the segment of vessel or hollow organ being treated.

Figure 3:
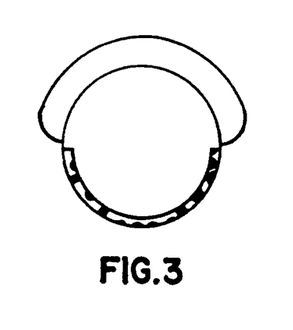
FIG. 3 is a cross-sectional view of an embodiment of the present invention having a small balloon.
Figure 4:
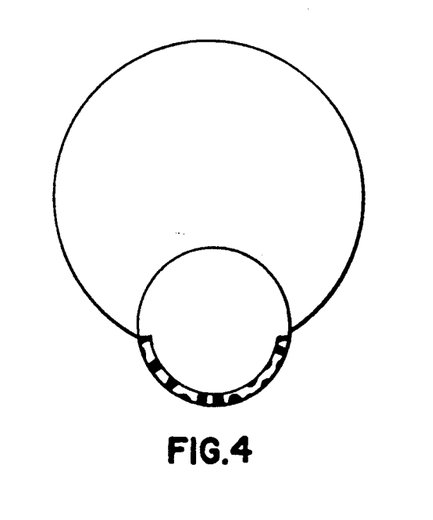
FIG. 4 is a cross-sectional view of an embodiment of the present invention having a large balloon.

The size (diameter and length) of the balloon, the size of the delivery region, and the ratio of balloon size to delivery area size would be variable and depend on the particular hollow organ, body vessel, or other localized tissue area, and the radial distribution of the diseased tissue which is to be treated. For example, preferred embodiments of the invention employ a hemiballoon structure having a partial circumference or angle of contact of about 60 to about 320 degrees, more preferably about 120 to 240 degrees, when inflated. Non-limiting examples of different size balloons for radially restricted drug delivery to a localized tissue are shown in FIGS. 3 and 4.

In the preferred embodiment, it is contemplated that the material from which the boundary layer or selectively permeable membrane of FIGS. 1 and 2 is constructed will be a semipermeable membrane material such as dialysis membrane (Cordis Dow 3500-cellulose acetate and Cordis Dow cellulose regenerated from acetate; anisotropic polyacrylonitrile available from Ashaki Medical). It is contemplated, however, that various other permeable, microporous or semipermeable materials may also be used including, without limitation, cellulose, cellulose acetate, polyvinyl chloride, polysulfone, polyacrylonitrile, silicon, polyurethanes, natural and synthetic elastomers. Examples of suitable microporous membranes are polyester, polyolefin, a fluorpolymer, or the like having pore sizes smaller than 1 micron and preferably from about 10 Å to 1 micron, with a nominal pore size of about 150 Å.

In the embodiments of FIGS. 1 and 2, pressure can be employed as a force to transport a fixative or other drug from the interior drug chamber 49 across the barrier layer 22 to an internal tissue, such as a vessel wall. When pressure is employed to drive a drug to a target area, regulation means known to those skilled in the art (e.g., compressor, regulator or syringe pump) can be used to apply sufficient pressure to deliver the drug to the target area. Those of skill in the art will recognize that the pressure applied will be adequate to drive the drug across selectively permeable membrane 22 to the target area without further traumatization of the internal body tissue to be treated. Non-limiting example pressures are from about 1 to 90 p.s.i.

It is contemplated that other transport forces could also be used either with or in lieu of pressure to enhance or otherwise control the speed of drug transport. For example, one method could utilize DMSO as a carrier to transport a fixative or drug through the vessel wall. Other fluid diffusion enhancement compositions include propylene glycol, azone and ionic or non-ionic surfactants.

Another method could utilize iontophoresis technology. Such technology is known in the art and is commonly used in transdermal drug delivery. In general, iontophoresis technology uses an electrical potential or current across a semipermeable barrier to drive ionic fixatives or drugs or drag nonionic fixatives or drugs in an ionic solution. Iontophoresis can be useful in certain applications of the present invention because it facilitates both transport of the fixative or drug across the selectively permeable membrane and enhances tissue penetration. In the application of iontophoresis, two electrodes, one on each side of the barrier, are utilized to develop the required potential or current flow. In particular, one electrode may be located inside of the catheter in opposed relation to the drug delivery wall of the catheter while the other electrode may be located at a remote site on a patient's skin. In addition to direct current, other wave forms may be utilized (e.g., a series of rectangular waves producing a frequency of 100 Hz or greater).

Another alternate drug transport force is phonophoresis (sometimes referred to as sonophoresis). Phonophoresis is the use of ultrasonic or high frequency sound waves to transport drugs. As used in the present invention, phonophoresis can be used to transport drugs through the selectively permeable membrane and into the surrounding tissue. For certain therapeutic procedures, phonophoresis has several advantages over iontophoresis, including the ability to achieve greater penetration and to more readily deliver an entire molecule, rather than an ionically charged form of the drug. All prior applications of phonophoresis have been limited to transdermal delivery of drugs. It has primarily been used to deliver anti-inflammatory agents and local anesthetics through the skin in treating epicondylitis, tendonitis, bursitis and osteoarthritis. It is also well-suited for driving fixatives or drugs across the catheter of this invention to localized body passageways or internal tissues because it facilitates both transport of a fixative or drug across the selectively permeable membrane and enhances tissue penetration. In addition to drug delivery, ultrasound may be advantageously used with the catheter of the present invention based on the increased tissue temperature, tissue hyperemia and increased capillary permeability associated with ultrasound. These actions can enhance intra-tissue drug transport and cellular uptake as well as cause vasodilation/relaxation which may be beneficial in vascular drug applications using catheter embodiments of the type described herein.

The embodiment of FIG. 5 illustrates a structure utilizing iontophoresis to assist in driving the fixative or other drug across the barrier layer 22 and into contact with the vessel walls 15. In FIG. 5, one electrode 28, the catheter electrode, is located on or within the catheter body 11 while the other electrode 31, the body surface electrode, is located on the body surface or within the body of the patient. In order for iontophoresis techniques to be utilized, the fixative or other drug within the drug chamber 49 requires specific characteristics. Ideally, such fixative or other drug should have an ionic nature or have other ionic molecules bound to the fixative or the active components of the drug to promote the iontophoretic movement or transport across the barrier layer 22. An electrical current for the iontophoretic process Of FIG. 5 is produced between the electrodes 28 and 31 by an external power source 30 through the electrical leads 29 and 33, respectively.

During operation of the device of FIG. 5, the apparatus is first Positioned adjacent the internal body tissue or vessel. The balloon interior 13 is then inflated with air or a fluid through the lumen 14. This is followed by activating the power supply 30, thereby creating a current between the electrode 28 and the electrode 31 which passes through the drug chamber 49. This current drives or drags the fixative or other drug within the chamber 49, across the wall 22, and into contact with the surrounding internal tissue or vessel wall 15. The structure of FIG. 5 utilizes iontophoresis as the driving force, although it is contemplated that iontophoresis can be utilized together with pressure, if desired.

It is contemplated that iontophoresis by itself, or in combination with a solvent like DMSO as a carrier, could yield fixative or drug transport into or through a vessel wall at pressures less than about 20 mm Hg above normal ambient vessel wall pressure and preferably at less than about 5 mm Hg, thereby avoiding substantial damage to the vessel wall known to occur at higher pressures.

The polarity of the iontophoretic electrodes may be reversed in order to recapture excess fixative or drug delivered to or through a radially restricted area of internal body tissue or vessel wall. In such case, an embodiment such as seen in FIG. 7 is preferred.

When phonophoresis is used as the active drug transport force, the cathode electrode 28 of FIG. 5 is replaced by an ultrasonic piezoelectric transducer (barium titanate, lead zirconate titanate, or the like), which is connected to the external power source 30 and placed within the catheter opposite the drug delivery wall. As seen in FIG. 8, the ultrasonic transducer is activated by the external power source (not shown) to enhance transport of drugs or fixatives into tissue surrounding the catheter. The diffusion rate of drugs delivered by phonophoresis depends upon the intensity and frequency of the ultrasonic field. Prior transdermal applications of phonophoresis use intensities of 0.1 to 6 watts/cm$^2$ and involve direct correlation between the amount of drug diffused and the intensity of the ultrasonic field. Internal applications (not requiring transdermal delivery) of phonophoresis with the catheter embodiments of the present invention are envisioned to require significantly less intensity to deliver an equal amount of drug. Various frequencies can be used. A frequency of about 1 MHz has been optimally used in transdermal phonophoresis. It is envisioned that approximately 1 MHz or less can be used for internal applications of the catheter embodiments described herein.

According to the present invention, catheter embodiments are envisioned employing a selectively permeable microporous membrane portion of the drug delivery component, together with an active, non-pressure, transport force for assisting the delivery of the drug to a body tissue. As described herein, in these embodiments the boundary layer 22 is a microporous membrane, which, in conjunction with the active delivery mechanisms, aids in controlling drug transfer from the catheter by minimizing passive diffusion or flow under the slight pressure involved in filling the drug chamber or inflating the balloon to make contact with a vessel wall. However, drug delivery into the tissue under active iontophoretic or phonophoretic delivery will not be inhibited by the membrane.

The microporous material provides more uniform delivery areas, which will provide more uniform drug distribution into the surrounding tissue, will reduce the potential for areas of high current densities during iontophoresis (associated with a few larger pores), and will decrease the potential for tissue damage or breakdown of the membrane material due to high current density.

The numerous micropores will reduce the likelihood that a significant portion of the membrane could become blocked with blood components, secretions, lubricants, or other material. In addition, blood or other secretions will not cross the microporous membrane and enter the drug chamber during deflation of the balloon. The microporous material will also allow rapid balloon deflation without blood reflux into the catheter, which is an important feature in coronary arterial applications. Finally, the microporous material will allow the use of a neutral or charged membrane surface to promote or control drug transfer and delivery.

Figure 6A:
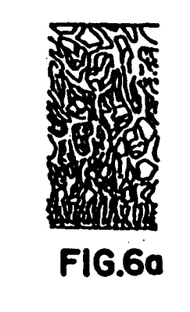
FIG. 6a shows an isotropic (asymmetric) structure.
Figure 6B:
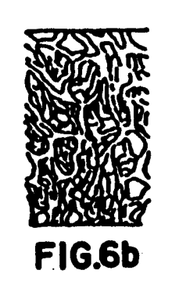
FIG. 6b shows a symmetric structure.

In embodiments of the present invention employing a microporous material for selectively permeable membrane 22, the various pore size membranes can be employed by those skilled in the art based on the intended use of the drug delivery apparatus. A schematic structure for the microporous membrane is illustrated in FIGS. 6a and 6b. Particularly, the selectively permeable microporous membrane can have either an isotropic (asymmetric) or symmetric structure. The pore size of the membrane can vary from about 10 Å to 10,000 Å (i.e., 1 micron).

The microporous membrane that satisfies the requirements of the invention can be manufactured in any of several ways, most of which are readily understood by those skilled in the art of manufacturing microfiltration and ultrafiltration membranes. These techniques include, for example:

1. A phase inversion process in which an appropriate polymer solution is coagulated in a nonsolvent quench bath can be employed.
2. A thermal inversion process can be used whereby a polymer solution or mixture at elevated temperatures can be coagulated by a reduction in temperature, under controlled conditions, to form a microporous membrane.
3. A so-called track-etch process whereby a polymer film is bombarded by protons, electrons, radiation, etc. and then subsequently subjected to a controlled etching can be used as well.
4. A laser may be used to form holes or pores of the desired size in a polymeric material.

In both processes 1 and 2, conditions can result in either a symmetric or an asymmetric membrane being formed. Either type of membrane can be useful, although a preference may exist for one or the other in a given application. Any post-treatment of the membranes, such as irradiation, chemical grafting, coatings, etc. that would render the membrane more hydrophilic, fouling resistant, form a thin-film composite membrane or impart any other desirable properties would be a possible supplement to the above-mentioned formation processes. These processes are examples of methods that can be used to form a membrane of the desired properties. However, any additional methods that currently exist or that may become apparent that produce the desired membrane properties should also be included in the possible membrane formation mechanisms.

There are several forms or geometries into which these membranes can be made. A flat sheet membrane can be cast and then formed into a balloon shape or cylinder by gluing, sonic welding, etc. Additionally, a hollow fiber membrane can be spun or a tubular Membrane cast that can be used as is or processed into a balloon by blow molding or some other balloon-forming process. A third option is to cast the membrane directly into a balloon shape by spin-casting or some other process that allows the desired shape to be achieved. During this processing, a membrane support can be used if desired or required.

Referring to FIG. 7, a drug delivery apparatus in which the boundary layer 22, having a selectively permeable microporous membrane together with an iontophoretic driving force, is shown. In FIG. 7, the drug delivery apparatus includes an electrode 28 within the drug delivery chamber 49. Drug is delivered to the chamber 49 through a drug input lumen 45' and an input port 47. The embodiment shown in FIG. 13 further includes a drug recovery lumen 48 in fluid communication with the drug delivery component 49 through drug recovery port 46. In the embodiment of FIG. 7, the electrode wire/conductor 29 is positioned in drug influx conduit 45. However, it will be understood that a separate conductor lumen can be provided, if desired.

It will be understood that the embodiment in FIG. 7 can be constructed without a drug recovery lumen, if desired. Also, FIG. 7 shows a guide wire lumen 11 which may be omitted, depending on the intended medical use of the device, such as urological applications.

The embodiment in FIG. 8 illustrates a further embodiment of a drug delivery apparatus including a boundary layer 22 which is a selectively permeable microporous membrane and having a phonophoretic driving force including a transducer 28' which is connected by conductor 29' shown in drug influx lumen 45. Again, one of skill in the art will be able to provide a separate lumen for conductor lead 29', if desired. As in the case of FIG. 7, the drug delivery apparatus in FIG. 8 includes a drug delivery lumen 45' and lumen for the guide wire, which can be excluded depending on the intended use of the drug delivery apparatus.

As seen in FIG. 9, the drug delivery apparatus can be provided with circumferential retention lips 50 adjacent the proximal and distal ends of drug delivery area 41. The retention lips 50 create a seal to the area of internal tissue to be treated.

Use of the drug delivery apparatus of the present invention will be readily apparent to those skilled in the art from the written description contained herein. Briefly, the apparatus is first inserted into the area of internal body tissue to be treated. With the balloon portion 12 across from the internal body tissue area to be treated, the balloon 12 is then inflated by introducing air or an inflation fluid through balloon lumen 14 and inlet 17 into balloon chamber 13. During inflation, the outer surfaces of the balloon 12 press outwardly against the inner surfaces of the vessel wall 15. In the case of the embodiment seen in FIG. 9, the inflation of balloon 12 also directs circumferential lips 50 against the opposite side of the vessel wall 15 to seal off an area of internal body tissue for drug treatment. Upon completing inflation of balloon 12, a drug solution is introduced through input lumen 45 and port 47 into drug delivery chamber 49. The drug delivery area 41 of drug delivery chamber 49 is defined by circumferential lips 50. The drug or fixative within drug chamber 49 is then delivered through the barrier layer or selectively permeable membrane portion 22 of drug delivery area 41. Drug delivery across the selectively permeable membrane 22 is facilitated by an appropriate transport force. Circumferential lips 50 seal off the vessel area for treatment, the drug or fixative transported across the selectively permeable membrane 22 of drug delivery area 41 comes into direct contact with the vessel wall 15.

The present invention is well suited to deliver vessel fixatives such as glutaraldehyde, formaldehyde, acetylaldehyde, or ethel alcohol, as well as drugs to reduce vasomotor action (calcium antagonist), inflammatory response steroids, anti-platelet inhibitors, anti-coagulates, and anti-tumor drugs, including sensitizers and immunomodulator drugs, and antibiotics.

Although the description of the preferred embodiment and method have been quite specific, it is contemplated that various modifications could be made without deviating from the spirit of the present invention. Accordingly, it is intended that the scope of the present invention be dictated by the appended claims, rather than by the description of the preferred embodiment and method.

We claim:

1. A drug delivery apparatus having a distal end and a proximal end for radially restricted local delivery of a drug to internal body tissue comprising:
   (a) a flexible catheter for insertion into an internal target area of a body;
   (b) drug delivery means connected to said catheter for radially restricted delivery of a drug to said internal body tissue, said drug delivery means comprising:
      (1) a fluid delivery passageway and a drug delivery chamber proximate said distal end of said drug delivery apparatus, said drug delivery chamber having an outer wall with a selectively permeable outer membrane portion; and
      (2) a non-permeable balloon affixed to and surrounding a portion of said drug delivery chamber, said balloon, when inflated, securing said drug delivery chamber at an internal body tissue target area and radially restricting local delivery of said drug by providing intimate contact between said balloon and a portion of said internal body tissue; and
   (c) means for assisting the transport of said drug across said selectively permeable outer membrane.

2. A drug delivery apparatus according to claim 1 wherein said selectively permeable membrane is a perforated membrane.

3. A drug delivery apparatus according to claim 1 wherein said selectively permeable membrane is a semi-permeable membrane.

4. A drug delivery apparatus according to claim 1 wherein said selectively permeable membrane is a microporous membrane.

5. A drug delivery apparatus according to claim 4 wherein said microporous membrane has pores sized from about 10 Å to about 1 micron.

6. A drug delivery apparatus according to claim 4 wherein said microporous membrane has pores of about 150 Å.

7. A drug delivery apparatus according to claim 1 wherein said drug delivery means further includes a drug recovery lumen extending from said drug chamber to the proximal end of said flexible catheter.

8. A drug delivery apparatus according to claim 1 wherein said means for assisting transport of said drug is a phonophoresis means, including an ultrasonic transducer in said catheter.

9. A drug delivery apparatus according to claim 1 wherein said means for assisting transport of said drug is an iontophoresis means, including an electrode in said catheter.

10. The drug delivery apparatus according to claim 1 wherein said drug delivery chamber further includes circumferential lips immediately adjacent the proximal and distal ends of the drug delivery area that act to minimize movement of a drug beyond a segment of internal tissue to be treated.

11. A drug delivery apparatus according to claim 1 wherein said non-permeable balloon has an angle of contact with said tissue of about 120 to 240 degrees when inflated.

12. A drug delivery apparatus having a distal end and a proximal end for radially restricted local delivery of a drug to internal body tissue comprising:
   (a) a flexible catheter for insertion into an internal target area of a body;
   (b) drug delivery means connected to said catheter for radially restricted delivery of a drug to said internal body tissue, said drug delivery means comprising:
      (1) a drug delivery chamber proximate said distal end of said drug delivery apparatus, said drug delivery chamber having a drug delivery area with a selectively permeable outer membrane portion and circumferential lips immediately adjacent the proximal and distal ends of the drug delivery area that act to minimize movement of a drug beyond a segment of internal tissue, and a fluid delivery passageway extending from said drug delivery chamber to the proximal end of said catheter; and
      (2) a non-permeable balloon affixed to and surrounding a portion of said drug delivery chamber, said balloon, when inflated, securing said drug delivery chamber at an internal body tissue target area and radially restricting local delivery of said drug by providing intimate contact between said balloon and a portion of said internal body tissue; and
   (c) means for assisting the transport of said drug across said selectively permeable outer membrane without application of pressure.

13. A drug delivery apparatus according to claim 12 wherein said selectively permeable membrane is a perforated membrane.

14. A drug delivery apparatus according to claim 12 wherein said selectively permeable membrane is a semipermeable membrane.

15. A drug delivery apparatus according to claim 12 wherein said selectively permeable membrane is a microporous membrane.

16. A drug delivery apparatus according to claim 15 wherein said microporous membrane has pores sized from about 10 Å to about 1 micron.

17. A drug delivery apparatus according to claim 16 wherein said microporous membrane has pores of about 150 Å.

18. A drug delivery apparatus according to claim 12 wherein said drug delivery means further includes a drug recovery lumen extending from said drug chamber to the proximal end of said flexible catheter.

19. A drug delivery apparatus according to claim 12 wherein said means for assisting transport of said drug is a phonophoresis means, including an ultrasonic transducer in said catheter.

20. A drug delivery apparatus according to claim 12 wherein said means for assisting transport of said drug is an iontophoresis means, including an electrode in said catheter.

21. A drug delivery apparatus having a distal end and a proximal end for radially restricted local delivery of a drug to internal body tissue comprising:
   (a) a flexible catheter for insertion into an internal target area of a body;
   (b) drug delivery means connected to said catheter for radially restricted delivery of a drug to said internal body tissue, said drug delivery means comprising:
      (1) a drug delivery chamber proximate said distal end of said drug delivery apparatus, said drug delivery chamber having a drug delivery area with a selectively permeable microporous outer membrane portion and circumferential lips immediately adjacent the proximal and distal ends of the drug delivery area that act to minimize movement of a drug beyond a segment of internal tissue, and a fluid delivery passageway extending from said drug delivery chamber to the proximal end of said catheter, and a drug recovery lumen extending from said drug chamber to the proximal end of said flexible catheter; and
      (2) a non-permeable balloon affixed to and surrounding a portion of said drug delivery chamber, said balloon, when inflated, securing said drug delivery chamber at an internal body tissue target area and radially restricting local delivery of said drug by providing intimate contact between said balloon and a portion of said internal body tissue; and
   (c) means for assisting the transport of said drug across said selectively permeable outer membrane without application of pressure.

* * * * *